United States Patent [19]

Shimizu et al.

[11] Patent Number: 4,659,840
[45] Date of Patent: Apr. 21, 1987

[54] METHOD FOR PREPARING DIARYL IODONIUM SALTS

[75] Inventors: Isoo Shimizu; Yasuo Matsumura, both of Yokohama; Yoshihisa Inomata, Kawasaki, all of Japan

[73] Assignee: Nippon Petrochemicals Co., Ltd., Tokyo, Japan

[21] Appl. No.: 587,556

[22] Filed: Mar. 8, 1984

[30] Foreign Application Priority Data

Mar. 9, 1983 [JP] Japan ................. 58-37315

[51] Int. Cl.$^4$ ................. C07D 207/407; C07D 25/00
[52] U.S. Cl. ................. 548/549; 570/206; 564/183; 564/184; 568/647; 568/938
[58] Field of Search ................. 548/549; 570/206; 564/183, 184; 568/647, 938

[56] References Cited

U.S. PATENT DOCUMENTS 4,151,175  4/1979  Crivello et al. ................. 570/206 X

FOREIGN PATENT DOCUMENTS 0119068  9/1984  European Pat. Off. ............ 570/206
1475361  2/1967  France .

OTHER PUBLICATIONS

Beringer et al., JACS, 81, pp. 342–351 (1959).

*Primary Examiner*—Glennon H. Hollrah
*Assistant Examiner*—D. B. Springer
*Attorney, Agent, or Firm*—Scully, Scott, Murphy & Presser

[57] ABSTRACT

Provided is a method for preparing diaryl iodonium salts represented by the formula:

$$[Ar_1-I^{\oplus}-Ar_2]HSO_4^{\ominus}$$

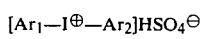

wherein $Ar_1$ and $Ar_2$ respectively are an aryl group which may be substituted with an electron donor group and which may be the same or different which comprises subjecting a compound represented by the formula $Ar_1$—H wherein $Ar_1$ is as defined above and a compound $Ar_2$—I wherein $Ar_2$ is as defined above to a coupling reaction in a sulfuric acid solution containing an oxidizing agent and diluted with a diluting agent to a concentration of 85% by weight or less at a reaction temperature in the range from −20° to +35° C.

6 Claims, No Drawings

METHOD FOR PREPARING DIARYL IODONIUM SALTS

BACKGROUND OF THE INVENTION

The present invention relates to a method for preparing diaryl iodonium salts.

Diaryl iodonium salts containing as a pair ion a halogenated metal represented by the general formula $$[Ar—I^{\oplus}—Ar']MX_n^{\ominus}$$

wherein Ar and Ar' are an aryl group, respectively, X is a halogen and n is an integer of 1 or more have drawn an attention in the art as an initiator for the photo polymerization of cation polymerizable monomers. Such compounds are prepared from a diaryl iodonium halide or a diaryl iodonium bisulfate.

Methods for preparing the halide heretofore proposed are such methods as (A) coupling of an aromatic hydrocarbon with an aryl iodide by the use of an oxidizing agent such as a persulfate;

(B) the coupling of an aromatic hydrocarbon by the use of a periodate, iodyl sulfate $[(IO)_2SO_4]$ or iodine acrylate $[I(OCOR)_3]$;

(C) coupling of the oxidized product of an aryl iodide with an aromatic hydrocarbon; and (D) the method by the use of an aryl lithium.

The method (A) above is described by Beringer et al. in J. Am. Chem. Soc. 81, 342 (1959). According to the method of Beringer et al., a coupling reaction of the iodine-substituted product such as nitrobenzene or benzoic acid with benzene is carried out in the presence of concentrated sulfuric acid and a persulfate, and an unsymmetric diaryl iodonium salt is recovered.

It was demonstrated by us, however, that when concentrated sulfuric acid was employed as in the above-mentioned method of Beringer et al. for a coupling reaction of an aromatic hydrocarbon substited with allyl or alkoxy group with an iodine-substituted derivative thereof, such reactions as sulfonation predominate to lower the yield of the diaryl iodonium salt. Also, the purity of diaryl iodonium salt thus obtained is very low and the purification is quite difficult. We have unexpectedly found that the reaction in a sulfuric acid solution diluted to a predetermined concentration is not accomplished by such reactions as sulfonation thereby improving the selectivity and giving a diaryl iodonium salt in a higher yield.

SUMMARY OF THE INVENTION

It is an object of the invention to provide an improved method for preparing diaryl iodonium salts.

Another object of the invention is to provide a method for carrying out a coupling reaction of an aromatic hydrocarbon, which may be substituted by the specified group, with an iodine-substituted derivative thereof at a high selectivity.

According to the present invention, there is produced diaryl iodonium salts represented by the general formula (I) below:

$$[Ar_1—I^{\oplus}—Ar_2]HSO_4^{\ominus} \qquad (I)$$

wherein $Ar_1$ and $Ar_2$ respectively are an aryl group which may be substituted with an electron donor group and which may be the same or different by subjecting an aromatic hydrocarbon, which may be substituted by an electron donor group, $Ar_1$—H and an iodine-substituted aromatic hydrocarbon, which may be substituted by an electron donor group, $Ar_2$—I to a coupling reaction in a sulfuric acid solution containing an oxidizing agent and diluted with a diluent to a concentration of 85% by weight or less at a reaction temperature in the range from $-20°$ to $+35°$ C.

DESCRIPTION OF THE PREFERRED EMBODIMENTS

The aromatic hydrocarbons or electron donor group-substituted aromatic hydrocarbons used in the invention are aromatic hydrocarbons having a condensed or non-condensed aromatic nucleus, for example, benzene, indane and naphthalene and derivatives of these aromatic hydrocarbons substituted on the aromatic nucleus with an electron donor group. The electron donor group includes $C_1$–$C_{12}$ alkyl groups such as methyl, ethyl, iso-propyl, n-propyl, iso-butyl, t-butyl and sec-butyl, cycloalkyl groups such as cyclohexyl, aryl groups such as phenyl, tolyl and naphthyl, alkoxy groups such as methoxy and ethoxy, N-substituted amino groups such as N,N-acetamino and succinamido and the like.

Taking benzene or its derivatives as an example, the aromatic hydrocarbon is represented by the following formula (II):

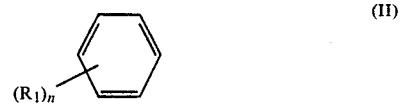
(II)

wherein n is an integer of 0 to 3, and each $R_1$ is hydrogen atom or an electron donor group as defined above.

Illustrative of the aromatic hydrocarbons or derivatives thereof of the formula (II) are benzene, alkylbenzenes such as toluene, ethylbenzene, isopropylbenzene, n-propylbenzene, iso-butylbenzene and t-butylbenzene, cyclohexylbenzene, biphenyl, alkoxybenzenes such as anisole and ethoxybenzene, N-substituted acylanilines such as acetanilide, N-phenylsuccinimide, N-phenylphthalimide and the like.

The iodine-substituted derivatives to be coupled with the aromatic hydrocarbons or derivatives thereof as mentioned above are those in which the aromatic nucleus of these aromatic hydrocarbons is substituted with iodine.

Also taking benzene or its derivatives as an example, it follows that they are represented by the formula (III) below:

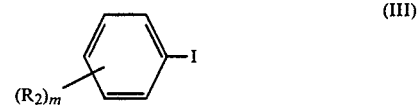
(III)

wherein m is an integer of 0 to 3, and each $R_2$ is a hydrogen atom or an electron donor group as defined above.

Illustrative of the iodine-substituted derivatives (III) are thus iodine-substituted derivatives of the hydrocarbons represented by the general formula (II).

Such iodine-substituted derivatives to be used as one of the starting materials in the present invention may be easily prepared by iodination of the corresponding aromatic hydrocarbons. Also, iodoaryls, which are by-products produced when diaryl iodonium salts mentioned below are reacted with unsaturated compounds in the presence of transition metal catalysts, may be used.

The aromatic hydrocarbons are coupled with the iodine-substituted aromatic hydrocarbons through an iodine atom.

The diaryl iodonium salts produced by the coupling are, therefore represented by the above-mentioned formula (I). Taking benzene or its derivatives as an example again, they are represented by the formula (IV):

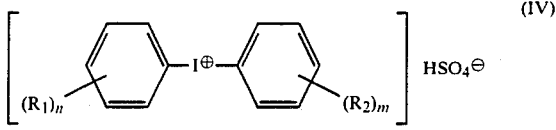

wherein $R_1$, $R_2$, m and n are as defined for the above-mentioned formulae (II) and (III).

Illustrative of the diaryl iodonium salts are salts of symmetric diaryl iodonium in which the two aryl groups are identical such as diphenyl iodonium, ditolyl iodonium, dixylyl iodonium, bis(iso-propylphenyl)iodonium as well as non-symmetric phenyl tolyl iodonium and phenyl xylyl iodonium.

The coupling reaction is accomplished in a sulfuric acid solution at a specified concentration. The sulfuric acid solution is prepared by diluting concentrated sulfuric acid or fuming sulfuric acid with a diluting agent to a predetermined concentration.

The diluting agent to be used may be any of liquids which are in nature miscible with concentrated sulfuric acid or fuming sulfuric acid and do not participate in the reaction. For example, it may be water, a fatty acid such as acetic acid, a fatty acid anhydride such as acetic acid anhydride or a mixture thereof.

It is critical in the present invention to employ a sulfuric acid diluted with a diluting agent such as mentioned above to a concentration of 85% by weight or lower. If the concentration of sulfuric acid exceeds the above-mentioned one, side reactions such as sulfonation will predominate with a result that the yield of the iodonium and the purity of the iodonium salts obtained will be reduced. Although no lower limit is set for the concentration, a concentration lower than 1% is undesirable because the reaction per se will hardly proceed. Dilution may be made to an appropriate concentration within the above-set scope depending upon the nature of the substituent. For example, where an aromatic hydrocarbon which is substituted with a substituent with a carbon atom directly bonded with the aromatic nucleus, the concentration is in the range from 40 to 85% by weight, preferably from 70 to 80% by weight. As such substituents are mentioned alkyl groups such as methyl, ethyl, iso-propyl, n-propyl, n-butyl, iso-butyl, sec-butyl and t-butyl, cycloalkyl groups such as cyclohexyl, phenyl group and the like. Where an aromatic hydrocarbon is substituted with a substituent with an atom having a lone pair electron such as oxygen atom or nitrogen atom directly bonded with the aromatic nucleus, sulfuric acid is used at a concentration in the range from 1 to 35% by weight, preferably from 2 to 20% by weight. Such substituents include alkoxy groups such as methoxy and ethoxy, N-substituted amide groups such as acetamido and succinimido and the like.

A variety of oxidizing agents may be employed. For example, salts of persulfuric acid with alkali metals such as potassium and sodium, its ammonium salt, peroxides of alkali earth metals such as barium peroxide and the like are used. They are used usually in an amount of about 1-3 moles per mole of aromatic hydrocarbons.

A mixture of a benzene, an iodine-substituted derivative and an oxidizing agent in a diluted sulfuric acid solution is reacted at a temperature in the range from $-20°$ to $+35°$ C. A reaction temperature higher than 35° C. will induce side reactions, and the reaction will not proceed at a temperature below $-20°$ C. Preferred reaction temperatures are in the range from $-15°$ to $+25°$ C. The reaction time may be appropriately selected and usually is several hours or longer.

The order of the components added in the present reaction is not critical. The reaction proceeds after addition in any order and mixing.

This reaction is highly para-oriented. For example, the reaction of toluene and p-iodotoluene selectively produces di(p-tolyl)iodonium salt.

The process of the invention carried out as described above affords a diaryl iodonium salt in a very high yield. The counter ion of the salt is bisulfate ion as shown in the formula below:

wherein $Ar_1$ and $Ar_2$ are defined above.

The counter ion can be exchanged with any anion. For convenience of separation, purification and use of the resulting diaryl iodonium salt for a further reaction, it is desirable to convert the bisulfate salt to a halogen salt.

The conversion is effected readily by subjecting an inorganic halide forming a halogen ion and the diaryl iodonium bisulfate obtained above.

The ion exchange may be easily conducted by adding an aqueous solution of inorganic halide or inorganic halogenated metal salt which produces anions such as halogenide or halogenated metal ion as mentioned below into an aqueous solution of diaryl iodonium bisulfate obtained.

The amount of the inorganic salt added is usually equivalent or more to the bisulfate, preferably 1.1 to 1.3 equivalent.

As the inorganic salt are mentioned alkali metal halides such as sodium chloride, potassium bromide and potassium iodide, ammonium halides such as ammonium chloride, ammonium bromide and ammonium iodide and the like.

As the halogenated metal salts are mentioned salts producing tetrahalogenated metal ions such as sodium tetrafluoroborate, ammonium tetrachlorozincate and potassium tetrachloropalladate, and salts producing hexahalogenated metal ions such as magnesium hexafluorosilicate and potassium hexafluorostanate.

The diaryl iodonium salts obtained in the present invention are industrially useful as photopolymerization catalysts and the like. Also, the present reaction can be used as economical synthetic means. If the present reaction is applied to a reaction in which iodine is by-produced and separated as an iodoaryl, expensive iodine can be used repeatedly. One of these reactions is a reaction of a diaryl iodonium salt in the presence of a transition metal catalyst. If styrene, carbon monoxide or acrylic acid is added in this reaction system, such as unsaturated compound bonds to the aromatic hydrocarbon residue in the iodonium salt. Also, in this case, iodine is separated from the iodonium salt as an iodoaryl. Therefore, the iodoaryl produced may be used as a starting material to produce a diaryl iodonium salt in a recycled manner without being lost, and consequently the above reaction becomes more economical.

The invention will be described in more details by means of examples. All parts in the examples are part by weight.

EXAMPLE 1

To a mixture of iodobenzene (40.8 parts), benzene (35 parts) and an aqueous sulfuric acid in an amount and at a concentration shown in Table 1 was added 82 parts of ammonium persulfate. The resulting mixture was stirred at −10° C. for 20 hours. To the reaction mixture was then added 400 parts of distilled water, followed by addition of a solution of 30 parts of potassium bromide in 200 parts of distilled water. Stirring of the mixture for 30 minutes produced precipitates of the product, which were filtered, washed with water and then with ether and dried under reduced pressure at 50° C. There was obtained a solid product. Analyses were done by NMR spectrum, IR spectrum and liquid chromatography, and the yield was determined in terms of diphenyl iodonium bromide. Results are also shown in Table 1.

All of the products were pale yellow solids except for the product in Run No. 1 which was deep black. In Run No. 5, there was formed no precipitate with unreacted iodobenzene and benzene recovered. The yield in Run No. 6 represented the one from the reaction conducted at 5° C.

In this and subsequent examples the yield was determined by analysis for a bromide or iodate product formed by ion exchange of the whole of the diaryl iodonium bisulfate initially formed with potassium bromide or potassium iodide. The diaryl iodonium salt itself underwent no change in the ion exchange.

TABLE 1

| Run No. | Concentration of Sulfuric acid (% by weight) | Aqueous sulfuric acid (Part) | Yield (%) |
|---|---|---|---|
| 1 | (Concentrated sulfuric acid) | 250 | 5 |
| 2 | 80 | 312 | 94 |
| 3 | 73.5 | 325 | 96 |
| 4 | 65 | 385 | 16 |
| 5 | 38 | 658 | — |
| 6 | 73.5 | 325 | 79 |

The same procedures as mentioned above were repeated except that m-iodobenzoic acid or m-iodonitrobenzene was used in place of iodobenzene. In those cases the reaction of the present invention scarcely proceeded, and sulfonation reaction preferentially proceeded instead except that a concentrated sulfuric acid was used.

EXAMPLE 2

The procedures were the same as in Example 1 except that a sulfuric acid solution diluted with acetic anhydride to a concentration of 70% by weight was employed in place of the 73.5% aqueous sulfuric acid used in Example 1 (Run No. 3). There was obtained diphenyl iodonium bromide in a yield of 85%.

EXAMPLE 3

The procedures were the same as in Example 1 except that a sulfuric acid solution diluted with glacial acetic acid to a concentration of 55% by weight was employed in place of the 73.5% aqueous sulfuric acid used in Example 1 (Run No. 3). There was obtained diphenyl iodonium bromide in a yield of 90%.

EXAMPLE 4

To a mixture of p-iodotoluene (10.85 parts) and toluene (18.4 parts) in 83.5 parts of a 73.5% by weight aqueous sulfuric acid was 20.5 parts of ammonium persulfate. The resulting mixture was treated in the same way as in Example 1. There was obtained 20.5 parts of di(p-tolyl)iodonium bromide (yield 99.7%).

EXAMPLE 5

To a mixture of iodoanisole (47 parts), anisole (43 parts) and an acetic acid solution of sulfuric acid in an amount and at a concentration shown in Table 2 was added 82 parts of ammonium persulfate. The resulting mixture was stirred at 20° C. for 50 hours. The reaction mixture was treated in the way as in Example 1 except that the potassium bromide used therein was replaced by potassium iodide. There was produced a solid product which was confirmed to be bis(p-methoxyphenyl)iodonium iodide.

All of the products were yellow powders except for the product in Run No. 7 which was deep black. There was formed no precipitate formed with unreacted iodoanisole and anisole recovered.

TABLE 2

| Run No. | Concentration of sulfuric acid (% by weight) | Acetic acid solution of sulfuric acid (part) | Yield (%) |
|---|---|---|---|
| 7 | 40 | 660 | 3 |
| 8 | 30 | 830 | 16 |
| 9 | 10 | 940 | 51 |
| 10 | 5 | 1000 | 75 |
| 11 | 1 | 1000 | — |

EXAMPLE 6

Aromatic hydrocarbons (1.0 mole) and iodine-substituted aromatic hydrocarbons (2.2 mole parts each) shown in Table 3 were mixed with sulfuric acid (12 mole) and solvents or ion exchanged water to dilute to the concentrations shown in Table 3, and ammonium persulfate (1.8 mole each) was mixed therewith and reaction was allowed to proceed for predetermined period of time. After completion of reaction, a solution of potassium bromide was added into the reaction system in the same manner as in Example 1 and diaryl iodonium bromide was recovered. The results are shown in Table 3.

TABLE 3

| Run No. | | Aromatic hydrocarbons | iodine-substituted compound |
|---|---|---|---|
| 12 | Example Comparative Example | 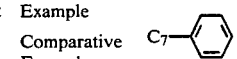 | 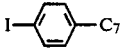 |
| 13 | Example Comparative Example | 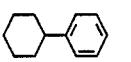 | 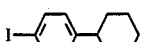 |
| 14 | Example Comparative Example | 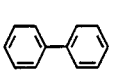 |  |

TABLE 3-continued

| Run No. | | | Concentration of sulfuric acid (Solvent) | Temperature Reaction Time | Yield (%) | State or Melting Point (°C.) of Diaryl iodonium bromide |
|---|---|---|---|---|---|---|
| 15 | Example | 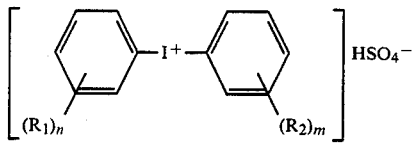 | | | | |
| | Comparative Example | | | | | |
| 16 | Example | $CH_3-$⟨phenyl⟩    $I-$⟨phenyl⟩ | | | | |
| | Comparative Example | | | | | |
| 12 | Example | 80% (acetic anhydride) | −5° C. 20 hrs. | 89 | pale yellow paste |
| | Comparative Example | 95% (acetic anhydride) | | 35 | blackish brown sludge |
| 13 | Example | 75% (water) | 5° C. 20 hrs. | 93 | pale yellow powder |
| | Comparative Example | 90% (water) | | 33 | blackish brown powder |
| 14 | Example | 70% (acetic acid) | 0° C. 15 hrs. | 85 | pale yellow powder |
| | Comparative Example | 95% (acetic acid) | | 0 | — |
| 15 | Example | 10% (acetic acid) | 15° C. 50 hrs. | 65 | yellow powder |
| | Comparative Example | 90% (acetic acid) | | 0 | — |
| 16 | Example | 75% (water) | 5° C. 20 hrs. | 93 | pale yellow powder |
| | Comparative Example | conc. sulfuric acid | | 10 | black powder |

What is claimed is:

1. In a process for preparing diaryliodonium bisulfate salts of the formula:

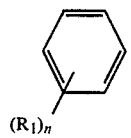

by coupling an aryl compound of the formula:

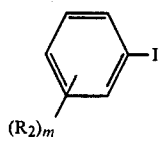

with an iodoaryl compound of the formula:

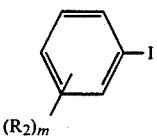

in the presence of an oxidizing agent wherein $R_1$ is hydrogen, $C_1$–$C_{12}$ alkyl, $C_3$–$C_{12}$ cycloalkyl, phenyl, naphthyl or $C_1$–$C_{12}$ alkyl substituted phenyl or naphthyl;

$R_2$ is hydrogen, $C_1$–$C_{12}$ alkyl, $C_3$–$C_{12}$ cycloalkyl, $C_1$–$C_{12}$ alkoxy, phenyl, naphthyl, $C_1$–$C_{12}$ alkyl substituted phenyl, $C_1$–$C_{12}$ alkyl substituted naphthyl, N,N-di($C_1$–$C_{12}$ alkanoyl)amine group or $C_1$–$C_{12}$ alkane dicarboximido group; and m and n are independently integers from 1–3;

the improvement comprising, adding directly to the aryl and iodoaryl compounds an oxidizing agent selected from the group consisting of persulfates and peroxides of alkali earth metals and ammonium salts and sulfuric acid in sufficient concentration to effect the formation of the diaryliodonium salt, said concentration of sulfuric acid being in the range from about 40% to about 85% by weight.

2. The process according to claim 1 wherein the concentration of sulfuric acid is in the range from about 70% to about 80% by weight.

3. The process according to claim 1 wherein the aryl and iodoaryl compounds, the oxidizing agent and the sulfuric acid are reacted at a temperature in the range from about −20° C. to about 35° C.

4. In a process for preparing diaryliodonium bisulfate salts of the formula:

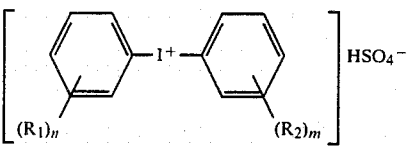

by coupling an aryl compound of the formula:

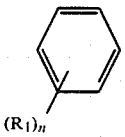

with an iodoaryl compound of the formula:

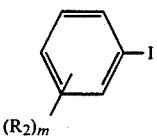

wherein $R_1$ is $C_1$–$C_{12}$ alkoxy, N,N-di($C_1$–$C_{12}$ alkanoyl)amino group or $C_1$–$C_{12}$ alkane dicarboximido group;

$R_2$ is hydrogen, $C_1$–$C_{12}$ alkyl, $C_3$–$C_{12}$ cycloalkyl, $C_1$–$C_{12}$ alkoxy, phenyl, naphthyl, $C_1$–$C_{12}$ alkyl substituted phenyl, $C_1$–$C_{12}$ alkyl substituted naphthyl, N,N-di($C_1$–$C_{12}$ alkanoyl)amino group or $C_1$–$C_{12}$ alkane dicarboximido group; and m and n are integers from 1–3;

the improvement comprising, adding directly to the aryl and iodoaryl compounds an oxidizing agent selected from the group consisting of persulfates and peroxides of alkali earth metals and ammonium salts and sulfuric acid in sufficient concentration to effect the formation of the diaryliodonium salt, said concentration of sulfuric acid being in the range from about 1% to about 35% by weight.

5. The process according to claim 4 wherein the sulfuric acid concentration is in the range from about 2% to 20% by weight.

6. The process according to claim 4 wherein the aryl and iodoaryl compounds, the oxidizing agent and the sulfuric acid are reacted at a temperature in the range from about −20° C. to about 35° C.

* * * * *